United States Patent [19]

Chauvel et al.

[11] Patent Number: 4,952,622

[45] Date of Patent: Aug. 28, 1990

[54] POLYMER PARTICLES WHICH CARRY, IMPLANTED ON THEIR SURFACE, AMPHIPHILIC MOLECULES CARRYING ION-FORMING OR REACTIVE GROUPS, A PROCESS FOR THE PREPARATION OF THESE PARTICLES AND THEIR USE IN BIOLOGICAL APPLICATIONS

[75] Inventors: Bernard Chauvel, Ermont; Jean-Claude Daniel, Fontenay/Sous/Bois; Christian Pusineri, Saint Symphorien D'Ozon, all of France

[73] Assignee: Rhone Poulenc Chimie, Courbevoie Cedex, France

[21] Appl. No.: 191,259

[22] Filed: May 6, 1988

[30] Foreign Application Priority Data

May 11, 1987 [FR] France ............................. 87/06549

[51] Int. Cl.$^5$ ........................... C08K 9/00; C08K 5/06
[52] U.S. Cl. .................................... 524/376; 523/205; 523/207; 524/556; 524/567; 524/568; 524/571; 524/577; 524/804; 526/302; 526/310; 526/311; 526/217; 526/292.3; 526/274; 526/286; 526/287; 526/317.1
[58] Field of Search ............... 523/205, 207; 524/376, 524/217, 302, 556, 567, 568, 571, 577; 526/302, 310, 311, 217, 292.3, 274, 286, 287, 317.1

[56] References Cited

U.S. PATENT DOCUMENTS

| | | | |
|---|---|---|---|
| 2,461,920 | 2/1949 | Pratt | 528/280 |
| 4,157,323 | 1/1979 | Yen et al. | 522/84 |
| 4,217,344 | 8/1980 | Vanderberghe et al. | 424/62 |
| 4,358,388 | 11/1982 | Daniel et al. | |

OTHER PUBLICATIONS

Kirk–Othmer, Encyclopedia of Chemical Technology, 3rd Ed., vol. 8, pp. 910–912.

Primary Examiner—Joseph L. Schofer
Assistant Examiner—Mark D. Sweet
Attorney, Agent, or Firm—Finnegan, Henderson, Farabow, Garrett and Dunner

[57] ABSTRACT

Polymer particles which carry, implanted on their surface, amphiphilic molecules carrying ion-forming or reactive groups, and dispersions thereof, which may be prepared by contacting a latex of particles of a polymer having a glass transition temperature Tg greater than about 40° C., with an amphiphilic compound having an HLB greater than or equal to 10 and a molecular weight greater than or equal to 400. The contacting is carried out at a temperature within the glass transition zone of the polymer, until enmeshing of the polymer chains and of the hydrophobic blocks of the amphiphilic compound has been achieved. The hydrophilic block of the amphiphilic compound carries at least one ion-forming or reactive group. The particles and their dispersions are useful in biological applications.

8 Claims, No Drawings

POLYMER PARTICLES WHICH CARRY, IMPLANTED ON THEIR SURFACE, AMPHIPHILIC MOLECULES CARRYING ION-FORMING OR REACTIVE GROUPS, A PROCESS FOR THE PREPARATION OF THESE PARTICLES AND THEIR USE IN BIOLOGICAL APPLICATIONS

The present invention relates to polymer particles which carry, implanted on their surface, amphiphilic molecules carrying ion-forming or reactive groups, the particles being as such or in aqueous dispersion.

The present invention also relates to a process for the preparation of these particles, and to their use in biological applications.

The polymer particles of the invention carry ion-forming or reactive groups sufficiently distant from the surface of the particles so as to be able to fix, onto these groups, bulky molecules such as proteins without danger of modifying the activity of the bulky molecules by contact with the macromolecular surface.

The polymer particles of the invention are defined in that they carry, implanted on their surface, molecules of an amphiphilic compound of HLB greater than or equal to 10 and of molecular weight greater than or equal to 400, these molecules comprising a hydrophilic oligomer block terminated by at least one ion-forming or reactive group, and a hydrophobic block enmeshed with the macromolecular chains of the polymer in the peripheral layer of the particles. The quantity of amphiphilic molecules implanted preferably corresponds to about $10^{-5}$ to $10^{-1}$ mole, more preferably $10^{-4}$ to $10^{-2}$ mole, per 100 g of polymer. The polymer constituting the polymer particles has a glass transition temperature $T_g$ above about 40° C., and preferably above about 70° C.

The diameter of the polymer particles is preferably on the order of 0.01 to 50 microns, more preferably on the order of 0.1 to 15 microns, most preferably, on the order of 0.3 to 5 microns.

Polymers which may constitute the polymer particles include homopolymers or copolymers comprising units derived from:

vinylaromatic monomers (such as styrene and vinyltoluene);

alkyl esters of $\alpha$, $\beta$-unsaturated acids (such as methyl- and ethyl- acrylates and methacrylates); unsaturated esters of carboxylic acids (such as vinyl acetate);

vinyl chloride and vinylidene chloride; dienes (such as butadiene); or monomers possessing nitrile functional groups (such as acrylonitrile).

The surface-implanted amphiphilic compounds preferably have an HLB greater than or equal to 10 and less than 20. They may have a hydrophilic oligomer block such as, for example, a polyoxyalkylene block comprising from 5 to 100, preferably 5 to 50, $C_2$-$C_3$ oxyalkylene units, or a polycarboxyethylene and/or polyamidoethylene and/or polycyanoethylene block comprising from 4 to 50 carboxyethylene and/or amidoethylene and/or cyanoethylene units. The latter units may have the structure —[$CHR_1$—$CHR_2$]—, wherein $R_1$ is hydrogen or $R_2$, and $R_2$ is —COOH, —$CONH_2$ or —CN. The hydrophilic oligomer block is terminated by at least one ion-forming or reactive group.

Exemplary ion-forming or reactive terminal groups include the following:

—OH, —$SO_3H$, —COOH, —CHO, —$\phi CH_2Cl$, —$NH_2$, —$NR_2$, —$NR_3 \oplus$ (R being a $C_1$—$C_2$—alkyl radical), —$CONH_2$, —NH—$NH_2$, —NH—CO—NH—$NH_2$, —SH and

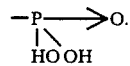

Exemplary amphiphilic compounds may include:

(a) polyoxyethylenated and/or polyoxypropylenated fatty alcohols or fatty acids, having 5 to 50 oxyalkylene units, and in which the hydrophobic block contains about 8 to 20 carbon atoms (such as the CEMULSOL DB products marketed by Societe Francaise d'Organo Synthese, and the SOPROPHOR LA products marketed by Rhone-Poulenc);

(b) the esters of such polyoxyethylenated and/or polyoxypropylenated fatty alcohols, carrying semicarbazide groups (such as the esters of such polyoxyethylenated and/or polyoxypropylenated fatty alcohols with para-methyl meta-semicarbazide phenylcarbamic acid), or carrying acid groups (such as the monoesters of such polyoxyethylenated and/or polyoxypropylenated fatty alcohols with azelaic acid) or carrying thiol groups (such as the esters of such polyoxyethylenated and/or polyoxypropylenated fatty alcohols with thioglycolic acid);

(c) the amides of such polyoxyethylenated and/or polyoxypropylenated fatty acids (such as the ETHOMID products marketed by Armour Industrial Chemical Co.);

(d) polyoxyethylenated and/or polyoxypropylenated alkylphenols having from 5 to 50 oxyalkylene units, and wherein the alkyl radical or radicals contains or contain from 8 to 12 carbon atoms, and their esters with phosphoric acid (such as the SOPROPHOR BC and OP products marketed by Rhone-Poulenc, the SOPROPHOR NFP products marketed by Geronazzo and the GAFAC RE products marketed by General Aniline and Film Corp.); and (e) polyoxyethylenated fatty amines wherein the hydrophobic block contains from 8 to 22 carbon atoms (such as the SOPROMINE products marketed by Rhone-Poulenc and the ETHOMEEN products marketed by Armour Industrial Co.).

The particles which form the subject of the invention may correspond to a certain size distribution or may be calibrated. The term "calibrated" is used herein to denote particles having a uniform particle size, such as those with a standard deviation of the diameter of less than about 5%.

One embodiment of the particles of the invention comprises magnetizable particles.

Such magnetizable polymer particles preferably comprise from 0.5 to 50% by weight, more preferably from 0.5 to 42% by weight, magnetic filler. Further preferred ranges include 0.5 to 35%, and especially 0.7 to 20%, by weight magnetic filler. The particles of the magnetic filler preferably have a size less than about 1 micron, more preferably between 0.002 and 0.05 micron. The magnetic filler is, of course, sufficiently fine to allow it to be included in the polymer particles.

Exemplary magnetic fillers may include:

(i) metals or their alloys (such as iron, iron-silicon, nickel, cobalt or their alloys with molybdenum, with chromium, with copper, with vanadium, with manganese, with aluminum or with titanium);

(ii) iron oxides (such as Fe or $\gamma$-Fe$_2$O$_3$), either pure or in combination with, or in a mixture with, other oxides (such as the oxides of cobalt, manganese, zinc, barium and the rare earths); and (iii) chromium dioxide.

The particles which form the subject of the invention can be obtained in accordance with a process comprising the following steps:

(1) contacting a latex of particles, the particles constituting the latex comprising a polymer having a glass transition temperature Tg greater than about 40° C and the particles having a diameter on the order of 0.01 to 50 microns, with an amphiphilic compound having an HLB greater than or equal to 10 and a molecular weight greater than or equal to 400, the amount of the amphiphilic compound employed corresponding to about $10^{-4}$ to 1 mole, preferably about $10^{-3}$ to $10^{-1}$ mole, per 100 g of polymer, wherein the contacting step is carried out at a temperature within the glass transition zone of the polymer, until enmeshing of the polymer chains and of the hydrophobic blocks of the amphiphilic compound is achieved, thereby implanting the amphiphilic compound on the particles; and (2) isolating the particles thus obtained.

Preferably, the process comprises the additional step, performed subsequent to step (1) and prior to step (2), of removing all, or substantially all, of the amphiphilic compound which has not been fixed by implantation.

The amphiphilic compounds which may be employed include those already mentioned above.

The latices which may be employed preferably comprise about 1 to 50%, more preferably 5 to 40%, most preferably 30 to 37%, by weight of polymer particles, the nature of which has already been indicated above. The particles have a diameter which is preferably on the order of 0.01 to 15 microns, more preferably on the order of 0.05 to 3 microns. The particles may correspond to a certain size distribution or may be calibrated.

If magnetizable particles are desired, the latices of magnetizable particles employed may be obtained in accordance with the processes described in European Patent No. 38,730 and U.S. Pat. No. 4,157,323, both incorporated herein by reference.

The amphiphilic compound and the latex are brought into contact by introducing the amphiphilic compound, optionally in aqueous solution, into the aqueous phase of the latex—for example, at ambient temperature—and then employing a temperature within the glass transition zone of the polymer constituting the latex—for example, by raising the temperature. In this temperature zone, the macromolecular chains acquire a certain mobility which allows them to enmesh with the hydrophobic part of the amphiphilic compound and to fix the said compound to the surface of the latex particles. This operation preferably takes about 15 minutes to 4 hours, more preferably, from 1 to 3 hours.

For a polystyrene latex, for example, this enmeshing operation is carried out at a temperature on the order of 70° to 80° C.

This temperature zone can be lowered, if desired, by additionally using plasticizers such as dialkyl phthalates, or aliphatic or aromatic hydrocarbons containing at least 5 carbon atoms.

Another means of lowering this temperature zone comprises carrying out the contacting step in the presence of a solvent for the amphiphilic compound and swelling agent for the polymer particles. The solvent facilitates the penetration of the amphiphilic compound by its hydrophobic part into the peripheral layer of the polymer particle, where it enmeshes with the polymer chains. The solvent can thereafter be removed—for example, by evaporation in vacuo.

Solvents which may advantageously be employed include aromatic compounds (such as toluene, ethylbenzene and xylenes), chlorinated aromatic compounds (such as monochlorobenzene, dichlorobenzene and trichlorobenzene), aliphatic and cyclic hydrocarbons (such as heptane, decane, cyclohexane and decalin), dialkyl ethers, alcohols (such as pentanol and cyclohexanol) and esters (such as methyl propionate).

Preferably, amphiphilic compound which does not become implanted during the contacting step, as well as any emulsifying constituent present beforehand in the latex, are subsequently removed by washing with water—for example, by ultrafiltration.

The polymer particles comprising the surface-implanted amphiphilic compound which are thus obtained may be separated from the aqueous medium by the conventional methods of sedimentation by centrifuging.

The present invention also relates to aqueous dispersions or latices of the polymer particles comprising, implanted on their surface, molecules of amphiphilic compound. The solids content of such dispersions is preferably from 1 to 50%, more preferably from 5 to 30%, most preferably from 10 to 15% by weight.

The latices may be prepared in accordance with known methods by direct dispersion of the particles in water.

A preferred embodiment of these latices is prepared by omitting step (2) of the process of the invention described above —especially, omitting separation of the particles from the medium in which the constituents have been brought into contact, after having performed the step of removal of any non-implanted amphiphilic compound.

The particles, or latices of the particles, which form the subject of the invention are particularly valuable in biological applications for fixing biological molecules (such as antibodies and antigens) by covalent bonds.

The fixing of biological molecules by covalent bonds onto the polymer particles can be carried out by a coupling reaction, which reaction involves the terminal groups of the implanted amphiphilic molecule and the functional groups of the biological molecule to be fixed.

This coupling reaction can be carried out in accordance with well-known methods, for example:

resorting to coupling agents (such as glutaraldehyde or a water-soluble carbodiimide), or by activation of the functional groups of the polymer (for example, by diazotization, by the action of cyanogen bromide or of hydrazine), followed by reaction with the molecule to be fixed.

The products can accordingly be used for carrying out diagnostic tests of the agglutination, radioimmunological and enzymatic type.

The examples which follow are illustrative and should not be considered as limiting the scope or spirit of the invention.

EXAMPLE 1

Implantation of CEMULSOL DB 25/18 (abbreviated AC-OH: an amphiphilic compound having an alcohol group), as the amphiphilic compound, on the particles of a calibrated polystyrene latex.

Empirical formula of the amphiphilic compound:

$$C_{18}H_{37}-O-CH_2-CH_2-{}_{50}OH$$

The HLB of CEMULSOL DB 25/18 is 17.8. (Methods for determining HLB are found in *Kirk-Othmer, Encyclopedia of Chemical Technology*, 3rd Edition, Volume 8, pp. 910–912, incorporated herein by reference. For example, for CEMULSOL DB 25/18, the % ethylene oxide is divided by 5, yielding the value 17.8 (that is, $[(2200/2470) \times 100] \div 5)$).

A 2% strength by weight solution of the amphiphilic compound in water is prepared.

50 g of this solution, corresponding to $4.05 \times 10^{-4}$ mole of amphiphilic compound, are mixed with 10 g of particles of a calibrated polystyrene latex of 0.9 micron mean diameter and 33% by weight solids content.

The mixture is stirred for 2 hours at 70° C.

After cooling, the latex obtained is washed by ultrafiltration, using 2.5 liters of purified water per 10 g of latex particles, so as to remove the non-implanted molecules of amphiphilic compound as well as the emulsifiers present in the starting latex.

The latex remains stable after ultrafiltration, this being a real index of the implantation of the amphiphilic compound.

The latex obtained is examined by nuclear magnetic resonance.

It is found that the amount by weight of amphiphilic compound implanted in 100 g of final particles is 6.4 g (theoretical amount=9.1 g).

The result is shown in Table I.

EXAMPLES 2 AND 3

The operation described in Example 1 is repeated under the same conditions, the 10 g of AC-OH being replaced by 5 g (Example 2) and 20 g (Example 3) of AC-OH, respectively. The result of the NMR determination is shown in Table I.

EXAMPLE 4

Implantation of CEMULSOL DB 25/18, as the, amphiphilic compound, on particles of a magnetizable polystyrene latex.

The operation described in Example 2 is repeated, replacing the calibrated polystyrene latex employed therein by 10 g of particles of a polystyrene latex having a solids content of 33%, these consisting of particles of diameter ranging from 0.5 to 0.9 micron, with a mean diameter of 0.7 micron and containing 41.5% by weight of $\gamma Fe_2O_3$ relative to the weight of the polymer. This mixture is treated as in Example 1.

The result of a conductimetric determination is shown in Table I.

EXAMPLE 5

Implantation of CEMULSOL DB 25/18 as the amphiphilic compound on the particles of a polyvinyl chloride latex.

The operation described in Example 1 is repeated, replacing the calibrated polystyrene latex employed therein by 10 g of particles of a calibrated polyvinyl chloride latex having a solids content of 37% by weight and consisting of calibrated particles of 0.7 micron mean diameter.

The mixture is stirred for 2 hours at 80° C. After cooling, the latex obtained is ultrafiltered.

The result of the conductimetric determination is shown in Table I.

EXAMPLE 6

Implantation of CEMULSOL DB 25/18 as an amphiphilic compound on the particles of a latex of a 40/60, by weight, styrene/methyl methacrylate copolymer.

The operation described in Example 1 is repeated, replacing the calibrated polystyrene latex employed therein by 10 g of particles of a calibrated latex of a 40/60 styrene/methyl methacrylate copolymer, having a solids content of 30% by weight and consisting of calibrated particles of 0.8 micron mean diameter.

The mixture is stirred for 2 hours at 90° C.

After cooling, the latex obtained is ultrafiltered.

The result of the NMR determination is shown in Table I.

EXAMPLE 7

Implantation of the ester of CEMULSOL DB 25/18 and paramethyl meta-semicarbazide phenylcarbamic acid (abbreviated ACSC: amphiphilic compound having a semicarbazide functional group) as the amphiphilic compound, on the particles of a calibrated polystyrene latex.

Empirical formula of the amphiphilic compound:

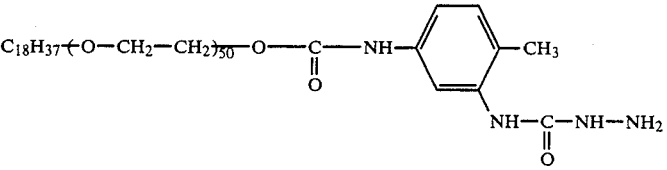

Preparation of the amphiphilic compound

The compound is prepared in two stages:

a first stage, consisting of functionalizing the CEMULSOL DB 25/18 by means of toluene diisocyanate in the presence of dioxane as the solvent, at a temperature of 90° C., and a second stage consisting of functionalizing the CEMULSOL DB 25/18 thus obtained by addition of hydrazine hydrate in the presence of dioxane at ambient temperature.

The desired amphiphilic compound is precipitated cold in diethyl ether.

Implantation

The operation described in Example 1 is repeated, replacing the CEMULSOL DB 25/18 by 50 g of an aqueous 2% strength solution of its derivative prepared as indicated above, this corresponding to $3.74 \times 10^{-4}$ mole of amphiphilic compound.

The result of the NMR determination is shown in Table II.

EXAMPLE 8

Implantation of the ester of CEMULSOL DB 25/18 and thioglycolic acid (abbreviated ACSH: amphiphilic compound having a thiol functional group) as the amphiphilic compound, on particles of a calibrated polystyrene latex.

Empirical formula of the amphiphilic compound:

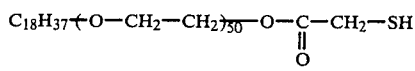

This compound can be prepared in accordance with the process described in U.S. Pat. No. 2,461,920, incorporated herein by reference.

The operation described in Example 1 is repeated, replacing the CEMULSOL DB 25/18 by 50 g of a 2% strength aqueous solution of its thioglycolic acid ester, of the above formula, corresponding to $3.93 \times 10^{-4}$ mole of amphiphilic compound.

The result of the conductimetric determination is shown in Table II.

EXAMPLE 9

Implantation of the ester of CEMULSOL DB 25/18 and paramethyl meta-semicarbazide phenylcarbamic acid (abbreviated ACSC) on particles of a latex of magnetizable polystyrene.

The operation described in Example 1 is repeated, replacing the calibrated polystyrene latex by 10 g of a polystyrene latex having a solids content of 33% consisting of particles of diameter ranging from 0.5 to 0.9 micron, with a mean diameter of 0.7 micron, and containing 41.5% by weight of $\gamma Fe_2O_3$ relative to the weight of polymer.

The mixture is treated as in Example 1.

The result of the conductimetric determination is shown in Table II.

EXAMPLE 10

Implantation of the monoester of CEMULSOL DB 25/18 and of azelaic acid (abbreviated AC-COOH: amphiphilic compound having an acid functional group), as the amphiphilic compound, on particles of a calibrated polystyrene latex.

Empirical formula of the amphiphilic compound:

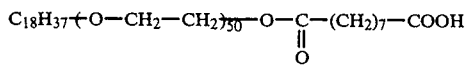

This compound can be prepared by esterification of CEMULSOL DB 25/18 with azelaic acid in pyridine in the presence of dicyclohexylcarbodiimide as the condensation agent.

The operation described in Example 1 is repeated, replacing the CEMULSOL DB 25/18 by 50 g of a 2% strength solution of its ester, of the above formula, corresponding to $3.79 \times 10^{-4}$ mole of amphiphilic compound.

The result of the NMR determination is shown in Table II.

EXAMPLE 11

Implantation of the ester of CEMULSOL DB 25/18 and of paramethyl meta-semicarbazide phenylcarbamic acid (ACSC) on a calibrated polystyrene latex in the presence of a swelling agent.

25 g of a 2% strength by weight solution of the amphiphilic compound in toluene is prepared.

10 g of an 0.1% strength by weight solution of ammonium laurate in water is prepared and is added to 10 g of particles of a polystyrene latex having a solids content of 33% by weight and consisting of calibrated particles of 0.8 micron diameter. The toluene solution of the amphiphilic compound is introduced into the latex. The mixture is kept at 45° C. for 2 hours, with stirring.

The toluene is removed by stripping at 70° C. under a pressure of 160 mm Hg in a rotary evaporator.

The latex is then washed by ultrafiltration.

The result of the NMR determination is shown in Table II.

EXAMPLE 12

The latex particles obtained in Example I are sedimented by means of a BECKMANN L 50 centrifuge equipped with a rotor 30 (apparatus marketed by BECKMANN) revolving at 10,000 rpm for 15 minutes, and are then dried in a vacuum oven at 40° C. and stored under nitrogen.

The properties of the particles are preserved.

The abbreviations relating to the starting polymer shown in Tables I and II have the following meaning:
PS:polystyrene
mag PS:magnetic polystyrene
PVC:polyvinyl chloride
P(S/MMA):copolymer of styrene and methyl methacrylate
SC:solids content In Tables I and II, "% Implanted" denotes weight % amphiphilic compound, relative to the weight of the final polymer implanted with amphiphilic compound.

TABLE I

| EXAMPLE | 1 | 2 | 3 | 4 | 5 | 6 |
|---|---|---|---|---|---|---|
| LATEX | | | | | | |
| polymer | PS | PS | PS | mag PS | PVC | P(S/MMA) |
| ø micron | 0.9 | 0.9 | 0.9 | 0.5–0.9 | 0.7 | 0.8 |
| SC % | 33 | 33 | 33 | 33 | 37 | 30 |
| AMPHIPHILIC COMPOUND | | | | | | |
| nature | AC—OH | AC—OH | AC—OH | AC—OH | AC—OH | AC—OH |
| g/100 g of polymer | 10 | 5 | 20 | 5 | 10 | 10 |
| moles/100 g of polymer | $4.05 \times 10^{-3}$ | $2.025 \times 10^{-3}$ | $8.1 \times 10^{-3}$ | $2.025 \times 10^{-3}$ | $4.05 \times 10^{-3}$ | $4.05 \times 10^{-3}$ |
| Temperature °C. | 70 | 70 | 70 | 70 | 80 | 90 |
| Duration, h | 2 | 2 | 2 | 2 | 2 | 2 |

TABLE I-continued

| EXAMPLE | 1 | 2 | 3 | 4 | 5 | 6 |
|---|---|---|---|---|---|---|
| % Implanted | | | | | | |
| theoretical | 9.1 | 4.8 | 16.7 | 4.8 | 9.1 | 9.1 |
| determined | 6.4 | 3.1 | 12.7 | 2.9 | 5.8 | 7.1 |

TABLE II

| EXAMPLE | 7 | 8 | 9 | 10 | 11 | 12 |
|---|---|---|---|---|---|---|
| LATEX | | | | | | |
| polymer | PS | PS | mag PS | PS | PS | PS |
| ∅ micron | 0.9 | 0.9 | 0.5–0.9 | 0.9 | 0.8 | 0.9 |
| SC % | 33 | 33 | 33 | 33 | 33 | 33 |
| AMPHIPHILIC COMPOUND | | | | | | |
| nature | ACSC | AC—SH | ACSC | AC—COOH | ACSC | AC—OH |
| g/100 g of polymer | 10 | 10 | 10 | 10 | 5 | 10 |
| moles/100 g of polymer | $3.74 \times 10^{-3}$ | $3.93 \times 10^{-3}$ | $3.74 \times 10^{-3}$ | $3.79 \times 10^{-3}$ | $1.87 \times 10^{-3}$ | $4.05 \times 10^{-3}$ |
| Temperature °C. | 70 | 70 | 70 | 70 | 45 | 70 |
| Duration, h | 2 | 2 | 2 | 2 | 2 | 2 |
| % Implanted | | | | | | |
| theoretical | 9.1 | 9.1 | 9.1 | 9.1 | 4.8 | 9.1 |
| determined | 5.3 | 4.8 | 3.1 | 6.2 | 4.3 | 6.4 |

We claim:

1. Polymer particles wherein amphiphilic molecules are enmeshed in the peripheral layer of said particles comprising:
   (a) particles of a homopolymer or a copolymer comprising units derived from vinylaromatic monomers, alkyl esters of alpha, beta-unsaturated acids, unsaturated esters of carboxylic acids, vinyl chloride, vinylidene chloride, dienes or monomers having nitrile functional groups, having a glass transition temperature Tg above about 40° C. wherein the macromolecular chains in the peripheral layer of the particles become mobile at a temperature within the glass transition zone; and
   (b) an amphiphilic compound having an HLB greater than or equal to 10, a molecular weight greater than or equal to 400 and a hydrophilic oligomer block terminated by at least one ion-forming or reactive group and a hydrophobic block, said hydrophobic block becoming enmeshed with the macromolecular chains of said polymer in the peripheral layer of said polymer particles, thus enmeshing said amphiphilic molecules on the surface of said polymer particles.

2. The particles of claim 1, wherein the quantity of said amphiphilic molecules implanted is from about $10^{-5}$ to $10^{-1}$ mole per 100 g of polymer.

3. The particles of claim 1, wherein the diameter of said particles is from 0.01 to 50 microns.

4. The particles of claim 1, wherein said amphiphilic compound has an HLB less than 20, the quantity of said amphiphilic molecules implanted is from about $10^{-4}$ to $10^{-2}$ mole per 100 g of polymer, said polymer has a Tg above 70° C. and the diameter of said particles is from 0.01 to 15 microns.

5. The particles of claim 1, wherein said hydrophilic oligomer block of said surface-implanted amphiphilic compound comprises a polyoxyalkylene block comprising from 5 to 100 $C_2$-$C_3$ oxyalkylene units or a hydrophilic polycarboxyethylene and/or polyamidoethylene and/or polycyanoethylene oligomer block comprising from 4 to 50 carboxyethylene and/or amidoethylene and/or cyanoethylene units, said hydrophilic oligomer block being terminated by at least one —OH, —SO$_3$H, —COOH, —CHO, —$\phi$CH$_2$Cl, —NH$_2$, —NR$_2$, —NR$_3 \oplus$ (R being a C$_1$—C$_2$—alkyl radical), —CONH$_2$, —NH—NH$_2$, —NH—CO—NH—NH$_2$, —SH, or

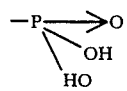

group.

6. The particles of claim 1, wherein said particles are magnetizable.

7. An aqueous dispersion of polymer particles, comprising from 1 to 50% by weight of the polymer particles of claim 1.

8. The aqueous dispersion of claim 7, wherein said dispersion comprises from 5 to 30% by weight of said particles.

* * * * *